United States Patent
Lawrence et al.

(10) Patent No.: US 11,994,025 B2
(45) Date of Patent: May 28, 2024

(54) BAND-STOP FILTER FOR VOLUME ANALYSIS OF DOWNHOLE PARTICLES

(71) Applicant: Halliburton Energy Services, Inc., Houston, TX (US)

(72) Inventors: Shaun Patrick Lawrence, Spring, TX (US); Mathew Dennis Rowe, Spring, TX (US)

(73) Assignee: Halliburton Energy Services Inc., Houston, TX (US)

( * ) Notice: Subject to any disclaimer, the term of this patent is extended or adjusted under 35 U.S.C. 154(b) by 183 days.

(21) Appl. No.: 17/748,909

(22) Filed: May 19, 2022

(65) Prior Publication Data
US 2023/0374897 A1 Nov. 23, 2023

(51) Int. Cl.
| | |
|---|---|
| E21B 49/00 | (2006.01) |
| E21B 21/01 | (2006.01) |
| E21B 43/08 | (2006.01) |
| E21B 43/34 | (2006.01) |
| E21B 47/002 | (2012.01) |
| E21B 47/003 | (2012.01) |

(52) U.S. Cl.
CPC ............ *E21B 49/005* (2013.01); *E21B 21/01* (2013.01); *E21B 43/08* (2013.01); *E21B 43/35* (2020.05); *E21B 47/002* (2020.05); *E21B 47/003* (2020.05)

(58) Field of Classification Search
CPC ....... E21B 47/00; E21B 21/065; E21B 49/005
See application file for complete search history.

(56) References Cited

U.S. PATENT DOCUMENTS

| | | |
|---|---|---|
| 9,651,468 B2 | 5/2017 | Rowe et al. |
| 9,759,645 B2 | 9/2017 | Rowe et al. |
| 9,857,289 B2 | 1/2018 | Rowe et al. |
| 10,145,229 B2 | 12/2018 | Galliano et al. |
| 11,015,404 B1 | 5/2021 | Shekhar et al. |
| 2012/0076364 A1 | 3/2012 | Tjhang et al. |
| 2014/0020954 A1 | 1/2014 | Pelletier et al. |
| 2014/0333754 A1 | 11/2014 | Graves et al. |
| 2015/0369731 A1* | 12/2015 | Taverner ............ G01N 21/4788 356/445 |
| 2016/0370274 A1 | 12/2016 | Rowe et al. |
| 2017/0153355 A1 | 6/2017 | Little et al. |

(Continued)

FOREIGN PATENT DOCUMENTS

WO 2021054840 3/2021

OTHER PUBLICATIONS

Halliburton Energy Services, Inc., International Search Report and Written Opinion, PCT/US2022/030112, Feb. 8, 2023, 11 pages.

*Primary Examiner* — Robert E Fuller
(74) *Attorney, Agent, or Firm* — Kilpatrick Townsend & Stockton LLP

(57) ABSTRACT

A system including an image acquisition unit in optical communication with a flow pathway. The system may include at least one illumination source directable toward a shale shaker. The illumination source may emit a light output. A band-stop filter may be affixed to the image acquisition unit to filter out infrared light. The band-stop filter may also allow electromagnetic radiation of the light output to reach the image acquisition unit. An analysis device may be used to determine a volume of downhole particles on the shale shaker using deflections of the light output observed by the image acquisition unit.

20 Claims, 4 Drawing Sheets

(56) References Cited

U.S. PATENT DOCUMENTS

| | | |
|---|---|---|
| 2019/0368287 A1 | 12/2019 | Shekhar et al. |
| 2019/0368347 A1 | 12/2019 | Kulkarni et al. |
| 2020/0332654 A1 | 10/2020 | Rowe et al. |
| 2020/0363289 A1 | 11/2020 | Shekhar et al. |
| 2021/0047911 A1 | 2/2021 | Rowe |
| 2021/0191252 A1 | 6/2021 | Macdonald et al. |

* cited by examiner

US 11,994,025 B2

BAND-STOP FILTER FOR VOLUME ANALYSIS OF DOWNHOLE PARTICLES

TECHNICAL FIELD

The present disclosure relates generally to wellbore drilling operations and, more particularly (although not necessarily exclusively), to determining volumes of downhole particles exiting a wellbore.

BACKGROUND

During the drilling of a hydrocarbon-producing well, a drilling fluid or "mud" is continuously circulated from a surface location down to the bottom of the wellbore being drilled and back to the surface again. The returning mud includes drill cuttings derived primarily from the formation being penetrated by a drill bit. Analyzing these drill cuttings can reveal information about the characteristics of the formation.

DETAILED DESCRIPTION

Figure 1:
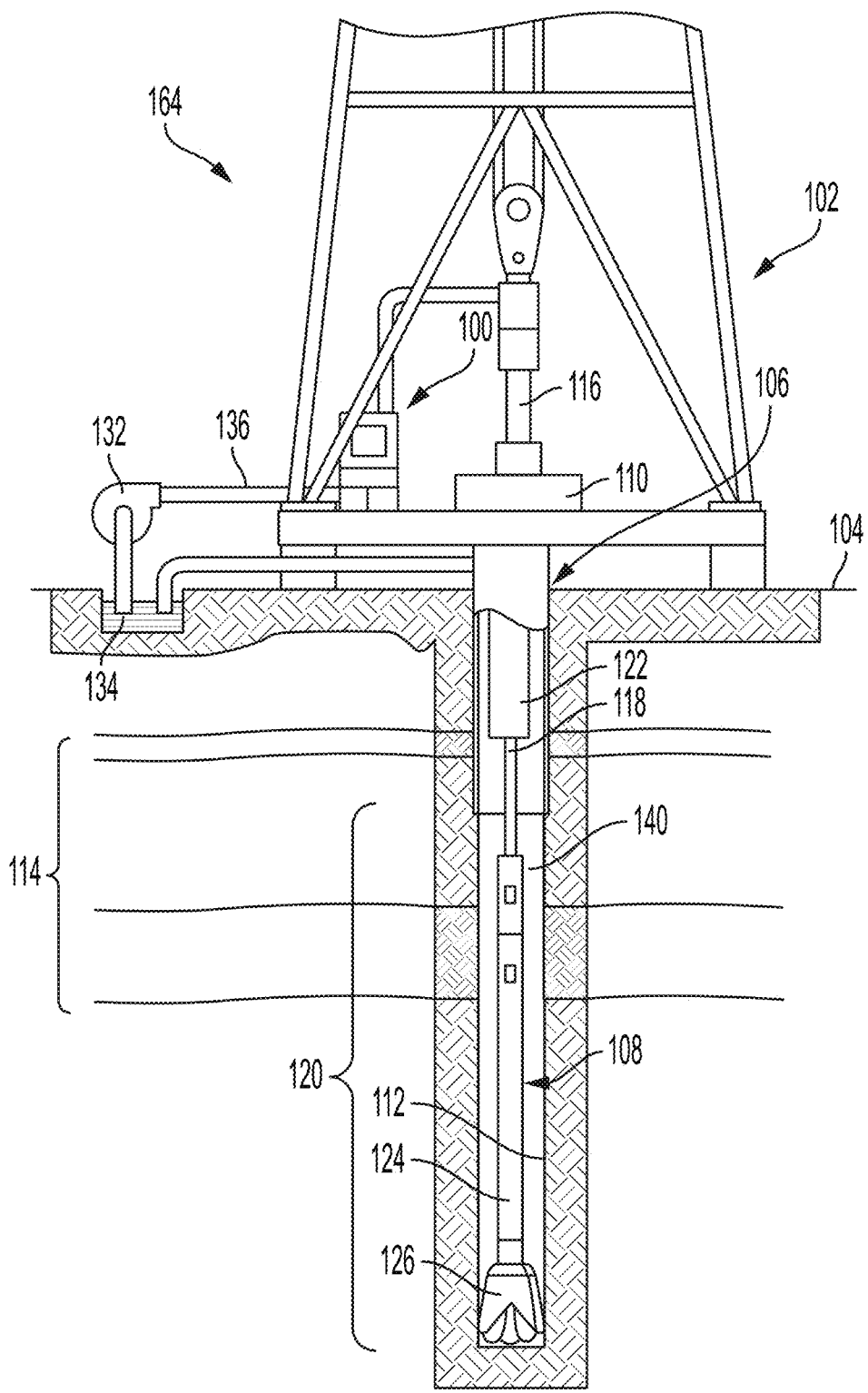
FIG. 1 is a schematic of a drilling system, according to some aspects of this disclosure.

Certain aspects and examples of the present disclosure relate to processing and analyzing downhole particles with deflections of light to determine a volume of the downhole particles. For example, the downhole particles can be drill cuttings returning to a surface in a drilling fluid from a downhole location during a drilling operation of a wellbore. The deflections of light can result from at least one illumination source casting light onto the downhole particles.

In an example, the deflections of light may be enhanced by use of a shale shaker that separates, through vibration, downhole particles from the drilling fluid. With the drilling fluid removed, the deflections of light may result only from interaction of the light with the downhole particles. A band-stop filter can be implemented with a light sensor, such as a camera, to exclude a selection of infrared and visible light while allowing the other infrared light deflections to pass into a lens of the camera. The deflections can be analyzed by a processing device in communication with the camera.

Implementing the band-stop filter with the camera may avoid performing imaging operations in an environment that is devoid of external light sources. In other words, the band-stop filter may be selected to filter out light originating from overhead light sources or natural light sources, for example. Thus, using the band-stop filter on the lenses of the camera could reduce costs and downtime resulting from setting up a "darkroom" environment to exclude light contamination from unintended light sources.

A band-stop filter may be added to a camera to limit the range of infrared light absorbed by the camera. Illumination sources, which may include lasers, may also be chosen to attenuate the frequency of infrared light passable through the band-stop filter and absorbed by the camera. The level of precision afforded by attenuating the frequency of infrared light absorbed by the camera may enable a process that analyzes downhole particles to determine a volume of particles exiting the wellbore.

On a shale shaker, a camera may be mounted above a screen along with one or more illumination sources that provide light across a width of the shaker. The velocity of particles crossing a screen of a shale shaker may be predetermined either from free-floating particles or with particles in the drilling fluid. In an example, the camera may include a band-stop spectrum filter, or a notch filter, that allows only a portion of the infrared spectrum to reach the lens. Use of the band-stop filter may enable accurate analysis while consistently implementing the wavelength from the illumination source throughout an imaging process. For example, based on the deflected light by the downhole particles, the analysis may involve determining a height and a width of the downhole particles. When the height and widths of the downhole particles are combined with velocity of the downhole particles, a volume of particles can be calculated. As drilling progresses, this technique can be used to determine a total volume of particles returning to the surface.

Illustrative examples are given to introduce the reader to the general subject matter discussed herein and are not intended to limit the scope of the disclosed concepts. The following sections describe various additional features and examples with reference to the drawings in which like numerals indicate like elements, and directional descriptions are used to describe the illustrative aspects, but, like the illustrative aspects, should not be used to limit the present disclosure.

FIG. 1 is a schematic of a drilling system 164, according to some aspects of this disclosure. The drilling system 164 contains a drilling rig 102 located at a surface 104 of a well 106. Drilling of oil and gas wells is commonly carried out using a string of drill pipes that couple to form a drilling string 108 that is lowered through a rotary table 110 into a wellbore 112.

The drilling rig 102 may provide support for the drill string 108. The drill string 108 may penetrate the rotary table 110 to drill the wellbore 112 through subsurface formations 114. The drill string 108 may include a kelly 116, drill pipe 118, and a bottom hole assembly 120, perhaps located at the lower portion of the drill pipe 118.

The bottom hole assembly 120 may include drill collars 122, a downhole tool 124, and a drill but 126. The drill but 126 may operate to create a wellbore 112 by penetrating the surface 104 and the subsurface formations 114. The downhole tool 124 may include any number of different types of tools including MWD tools, LWD tools, and others.

During drilling operations, the drill string 108, the kelly 116, the drill pipe 118, and the bottom hole assembly 120 may be rotated by the rotary table 110. In addition, the bottom hole assembly 120 may also be rotated by a motor (e.g., a mud motor) that is located downhole. The drill collars 122 may be used to add weight to the drill bit 126. The drill collars 122 may also operate to stiffen the bottom hole assembly 120, enabling the bottom hole assembly 120 to transfer the added weight to the drill bit 126, and in turn, to assist the drill bit 126 in penetrating the surface 104 and subsurface formations 114.

During drilling operations, a mud pump 132 may pump drilling fluid (sometimes known by those of ordinary skill in the art as "drilling mud") from a mud pit 134 through a hose 136 into a drill pipe 118 and down to the drill bit 126. The drilling fluid can flow out from the drill bit 126 and be returned to the surface 104 through an annular area 140 between the drill pipe 118 and the sides of the wellbore 112. The drilling fluid may then be returned to the mud pit 134, where such fluid is filtered. In some embodiments, the drilling fluid can be used to cool the drill bit 126, as well as to provide lubrication for the drill bit 126 during drilling operations. Additionally, the drilling fluid may be used to remove subsurface formation cuttings created by operating the drill bit 126. It is the images of these cuttings that many embodiments operate to acquire and process.

The system 164 may include a drilling mud screen to receive drilling mud, and one or more image processing systems 100. The image processing system 100 may have a field of view that includes a drilling mud screen, such as a shale shaker, and the image processing system 100 may include one or more image acquisition units, such as cameras, and one or more processors that control operation of the image processing system 100.

Figure 2:
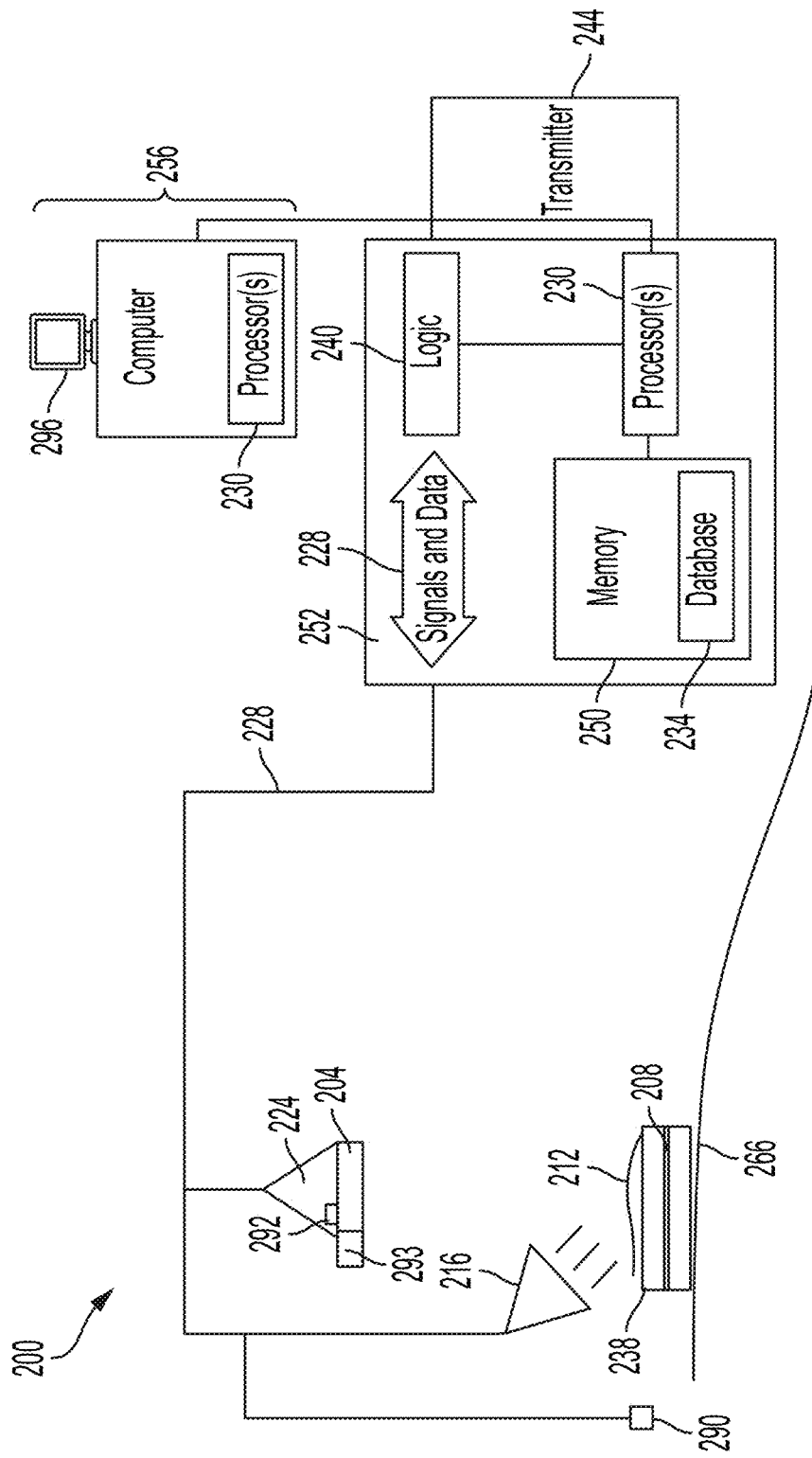
FIG. 2 is a block diagram of an example system for processing and analyzing of downhole particles, according to some aspects of this disclosure.

FIG. 2 is a block diagram of an example system for processing and analyzing of downhole particles, according to some embodiments. In many embodiments, a system 200 may include a combination of an image acquisition unit 224 and one or more processors 230. The system 200 may behave similarly to the image processing system 100 of FIG. 1. The image acquisition unit 224 or the processors 230 may be located above the surface 266 of a geological formation, perhaps forming part of a data acquisition system 252. In some embodiments, any of the components in FIG. 2 may be located below the surface 266.

The system 200 may include logic 240 that includes a programmable data acquisition subsystem. The logic 240 can be used to acquire live video stream information 228, and other data, such as information from downhole, including the depth of the drill bit during a drilling operation.

A memory 250, located above or below the surface 266, can be used to store acquired image data, as well as other data (e.g., in a database 134). The memory 150 may be communicatively coupled to the processor(s) 230.

In some embodiments, the image acquisition unit 224 may include one or more CCD (charge coupled device) cameras, including low light or infrared cameras, to be used in conjunction with one or more sources of illumination 216, such as white light, tungsten light, infrared light, or light emitting diodes (LEDs) to illuminate cuttings 212 deposited on a shaker 238 such as on a shaker screen 208 (also referred to herein as a "drilling mud screen 208"). The cameras may be focused on the shaker screen 208 to capture images of cuttings 212 as they move across one or more shakers 238.

The image acquisition unit 224 may have a band-stop filter 204 for filtering a selection of infrared and visible light. Using the band-stop filter may reduce costs and downtime from setting up a "darkroom" environment to exclude light contamination from unintended light sources. Commands to adjust either the wavelength of electromagnetic radiation emitted from the illumination source 216 or adjustments in the range of the band-stop filter 204 can complement each other such that the tunable band-stop filter may be adjusted to block electromagnetic radiation outside of the varying light output wavelengths of the illumination source 216.

In an example, a light detector 293 may be communicatively coupled with the data acquisition system 252. The light detector 293 may detect wavelengths of ambient light. Based on the detected wavelengths of the ambient light, the data acquisition system 252 can determine if the wavelengths of the ambient light are in the range of wavelengths blocked by the band-stop filter 204 or in the range of wavelengths provided by the illumination source 216 or the lasers 290 and 292. The data acquisition system 252 may adjust the band-stop filter 204, the illumination source 216, the lasers 290 and 292, or a combination thereof so that the band-stop filter 204 blocks the wavelengths of ambient light detected by the light detector 293 and does not block the wavelengths of the electromagnetic radiation generated by the illumination source 216, the lasers 290 and 292, or a combination thereof.

The image acquisition unit 224 can be connected to a data acquisition system 252, which may include the logic 240, and then to a computer (including one or more processors 230), or directly to a computer. The computer may use a three-dimensional (3D) face recognition program, a particle size analysis program, or both to measure and determine characteristics of the cuttings 212, such as size, volume, shape, etc. The live data can be analyzed in real-time to provide shape and size distribution, along with the volume of the cuttings 212 coming over the shaker 238.

The system 200 may also include one or more lasers. In this example, a laser 292 may be incorporated into the image acquisition unit 224 and positioned above the cuttings 212. The system 200 may also include a laser 290 positioned to a side of the cuttings 212. The system 200 can include more or fewer lasers. For example, the system 200 can include additional lasers at other positions relative to the cuttings 212. In some examples, the laser 290, the laser 292, or both may replace the illumination source 216. As part of the processing and analysis of the cuttings 212, the lasers 290, 292 can emit a coherent radiation into the cuttings 212. A line of the coherent radiation may deflect as a result of contacting particles of a detectable thickness. The distance between the original line of coherent radiation and the deflected line can be analyzed to determine the thickness of the particle(s) which cause the line of coherent radiation to deflect (e.g., through triangle properties). An actual surface area of the cuttings 212 can then be determined based on the captured coherent radiation.

A volume of the cuttings 212 can be obtained by multiplying the surface area of the cuttings 212 (determined by the laser 290 or 292 deflection) to the velocity of cuttings 212 passing over the laser line. The velocity of the cuttings 212 may be determined using an approach of tracking a particle over a certain distance for a certain amount of time. The image acquisition unit 224, in conjunction with a velocity capture algorithm can be used to track the velocity of the particle/cuttings 212. Other methods using radars may also be used to determine velocity of particles. Additionally, noise in the form of vibration on the shaker 238 may be filtered. This can be performed by mounting a reference target on a static portion of the shaker 238 and capturing the pixel movement using the image acquisition unit 224. An algorithm may be used to capture the pixel movement on the shaker 238. Other methods using accelerometers may also be used to baseline the vibrations on the shaker screen 208.

The illumination source 216 may include white lights for CCD cameras or near, mid, or far wave infrared lights, depending on the type of image acquisition unit 224 that is used. The illumination source 216 may be used to intensify the image. The image acquisition unit 224, such as a camera, can capture various images of the cuttings 214. The field of view, detection wavelength sensitivity, and resolution of the image acquisition unit 224 may be used to determine a number and type of devices 224 that are focused on the shaker 238.

Image acquisition units may include, for example, a pco 4000 CCD camera from Adept Turnkey Pty Ltd. with 4008×2672 pixel resolution for the visible light spectrum. If the conditions are such that a high sensitivity line scan camera may be useful, a Piranha HS-80-08K40 camera or Piranha HS-40-04K40 camera, also from Adept Turnkey Pty Ltd. can be used. For near infrared imaging, an XEVA-FPA-1.7-640 camera from LOT-Oriel Group Europe with an InGaAs array at 640×512 resolution can be used. For mid infrared imaging, a VarioTHERM® InSb camera from JENOPTIK Optical Systems Inc. with an InSb array at 640×512 resolution can be used. For far infrared detection, a Photon 640 camera from FLIR Systems, Inc. can be employed. Other devices can also be used.

The video stream information 228, or a processed form of the information, can be sent to a remote workstation 256 via coaxial cable or Ethernet cable. For longer data transmission distances, and to reduce the magnitude of possible interference, the video stream information 228 may be converted to an optical format and sent to the remote workstation 256 via fiber optic transmission. A transmitter 244 may be used to send the video stream information 228, or a processed form of the information, to the workstation 256 via wires, fiber optics, or wirelessly.

A three-dimensional face recognition engine can be used to identify more than just the general shape of the cuttings-the volume distribution of the cuttings can also be determined. The engine can be trained or modified to identify cutting shapes, to determine volume distribution, and to provide data in a form that various monitoring software, such as Halliburton's INSITE Anywhere® web delivery system, can process. These recognition and analysis programs include software that is similar to or identical to PAX-it image management and analysis software by MIS Inc, of Villa Park, IL, and Split-Online® automated digital image analysis system from Split Engineering LLC, as well as the SureMatch 3D facial recognition software suite available from Genex Technologies, Inc. of Bethesda, MD. Other software and processing instructions may be used, based on technical needs and flexibility.

The acquired video stream information 228 can be processed by programs similar to or identical to the INSITE Anywhere® web delivery system for real-time trend analysis. The processed data, which can be stored in the memory 250 (e.g., in the database 234), includes particle size distribution, particle shape distribution, and cutting volume. Thus, many embodiments may be realized.

For example, the system 200 may include an image acquisition unit 224 and one or more processors 230. The image acquisition unit 224 may acquire live video stream information 228 including image information of downhole cuttings. The processor(s) 230 may process the image information of the downhole cuttings to determine data that quantifies the shape, size distribution, or volume of the downhole cuttings. The processor(s) 230 may also publish changes in the data in conjunction with the probable conditions associated with a borehole drilling operation or a borehole fracturing operation.

Figure 3:
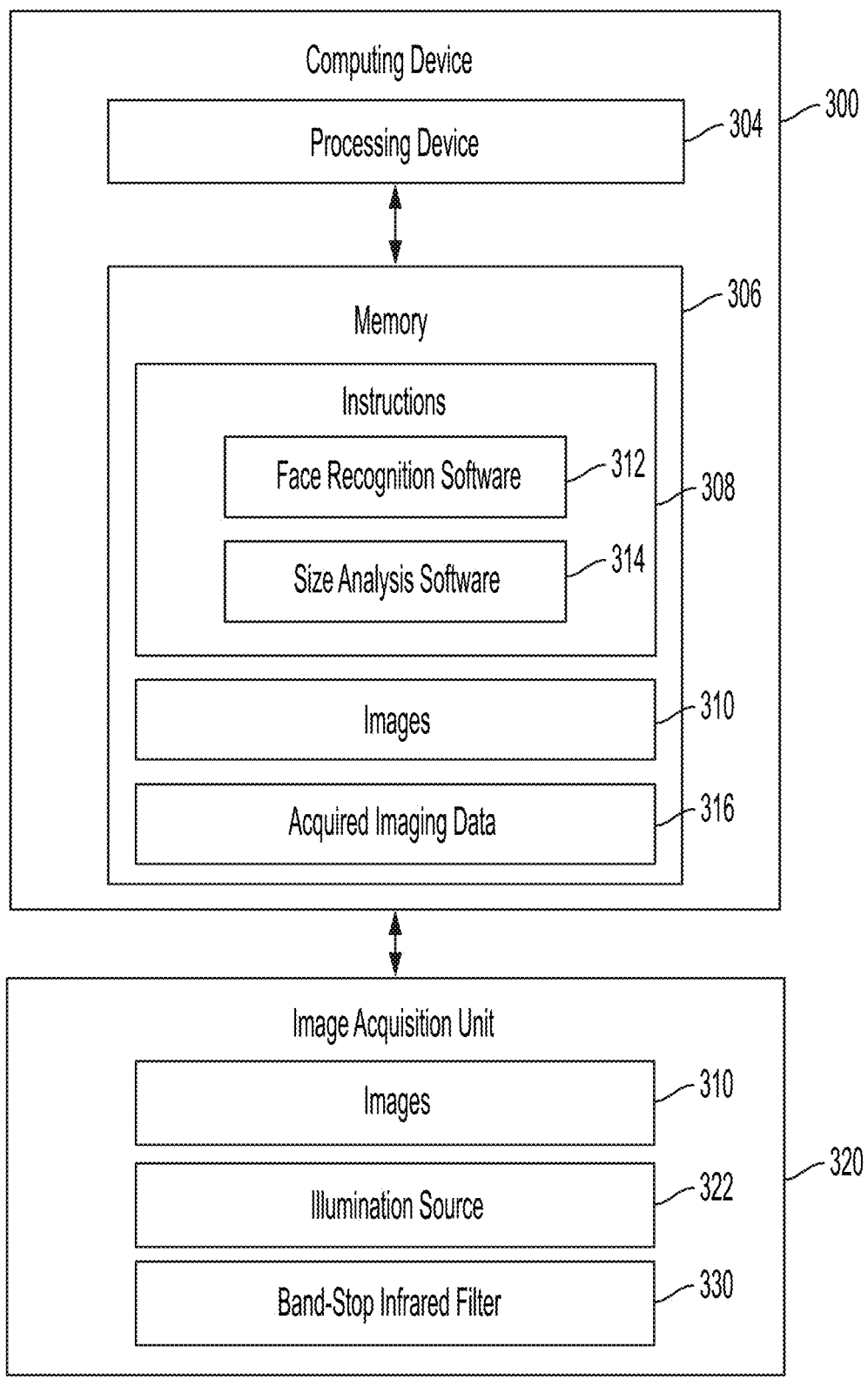
FIG. 3 is a block diagram of an example of a computing device containing instructions for implementing some aspects of the present disclosure, according to some aspects of this disclosure.

FIG. 3 is a block diagram of an example of a computing device 300 containing instructions 308 for implementing some aspects of the present disclosure. The computing device may be in operable communication with an image acquisition unit 320 similar to the image acquisition unit 224 of FIG. 2.

The instructions 308 can cause the computing device to acquire images 310 from the image acquisition unit 320 and other data, such as information from downhole, including the depth of a drill bit during a drilling operation. The acquired images 310 may behave similarly to the video stream 228 of FIG. 2. The instructions 308 can include commands to adjust the range of a tunable band-stop filter 330 affixed to the image acquisition unit 320, as well as commands to adjust an illumination source 322 affixed to or proximal to the image acquisition unit 320. The illumination source 322 may behave similarly to the illumination source 216 or the lasers 290 and 292 of FIG. 2. Commands to adjust either the wavelength of electromagnetic radiation emitted from the illumination source 322 or the range of the band-stop filter 330 can complement each other such that the tunable band-stop infrared filter 330 may be adjusted to block electromagnetic radiation outside of the varying light output wavelengths of the illumination source 322. The illumination source 322 may include a plurality of light sources. Electromagnetic radiation emitted from the illumination source 322 may be varied with instructions to either alter the emitted wavelength from a given light source amongst the plurality of light sources, activating and deactivating light sources amongst the plurality of light sources, or any combination therein.

A memory 306 can be used to store acquired image data 316, as well as other data. The memory 306 is communicatively coupled to the processing device 304. Instructions 308 may include a three-dimensional (3D) face recognition engine 312 or particle size analysis engine 314 to measure and determine characteristics of the downhole particles, such as size, volume, shape, etc.

The instructions 308 may include instructions to control an emission of coherent radiation from the illumination source 322, such as a laser. The instructions 308 may determine particle thickness based on an analysis of an original line of coherent radiation versus a deflected line of coherent radiation. A surface area of a particle may be determined by captured coherent radiation. A volume of the downhole particles can be obtained by multiplying the surface area of the downhole particles to the velocity of the downhole particles passing under the illumination source 322. The instructions 308 may include a velocity capture algorithm to be used in conjunction with the illumination source 322. In some examples, the instructions 308 may include operating instructions for a radar system to measure particle velocity. In some examples, the instructions 308 may cause the processing device 304 to use images 310 presented as video, similar to the video stream 228 of FIG. 2, in conjunction with the face recognition engine 312, the size analysis engine 314, or other suitable software to determine particle velocity.

The three-dimensional face recognition engine 312 can be used to identify more than just the general shape of downhole particles—the volume distribution of particles can also be determined. The software can be trained or modified to identify cutting shapes, to determine volume distribution, and to provide data in a form that various monitoring software, such as Halliburton's INSITE Anywhere® web delivery system, can process. The software can be modified to realize greater accuracy or fidelity in view of the band-stop infrared filter 330 affixed to the image acquisition unit.

The acquired image data 316 can be processed by programs similar to or identical to the INSITE Anywhere® web delivery system for real-time trend analysis. The processed data, which can be stored in the memory 306 can include particle size distribution, particle shape distribution, and cutting volume.

The instructions 308 may include commands for the computing device 300 to determine a projected volume of particles returning to a surface during drilling of a wellbore at a particular depth and over an amount of time. For example, the computing device 300 may determine the projected volume of particles returning to the surface based on a depth of the drill bit 126, the type of formation 114 at the depth, a rate of penetration of the drill bit 126, any other operational characteristics of the drilling operation, or any combination thereof. The instructions 308 may cause the processing device 304 to, in response to a determination that a difference between a measured volume and a projected volume exceeds an error threshold, output a notification of a downhole condition occurring. The instructions 208 may cause the processor to adjust a drilling operation based on the difference between the measured volume and the projected volume. In an example, the error threshold may be achieved when the measured volume is ten percent greater than or ten percent less than the projected volume. Other difference ranges between the measured volume and the projected volume may also be used as the error threshold.

Figure 4:
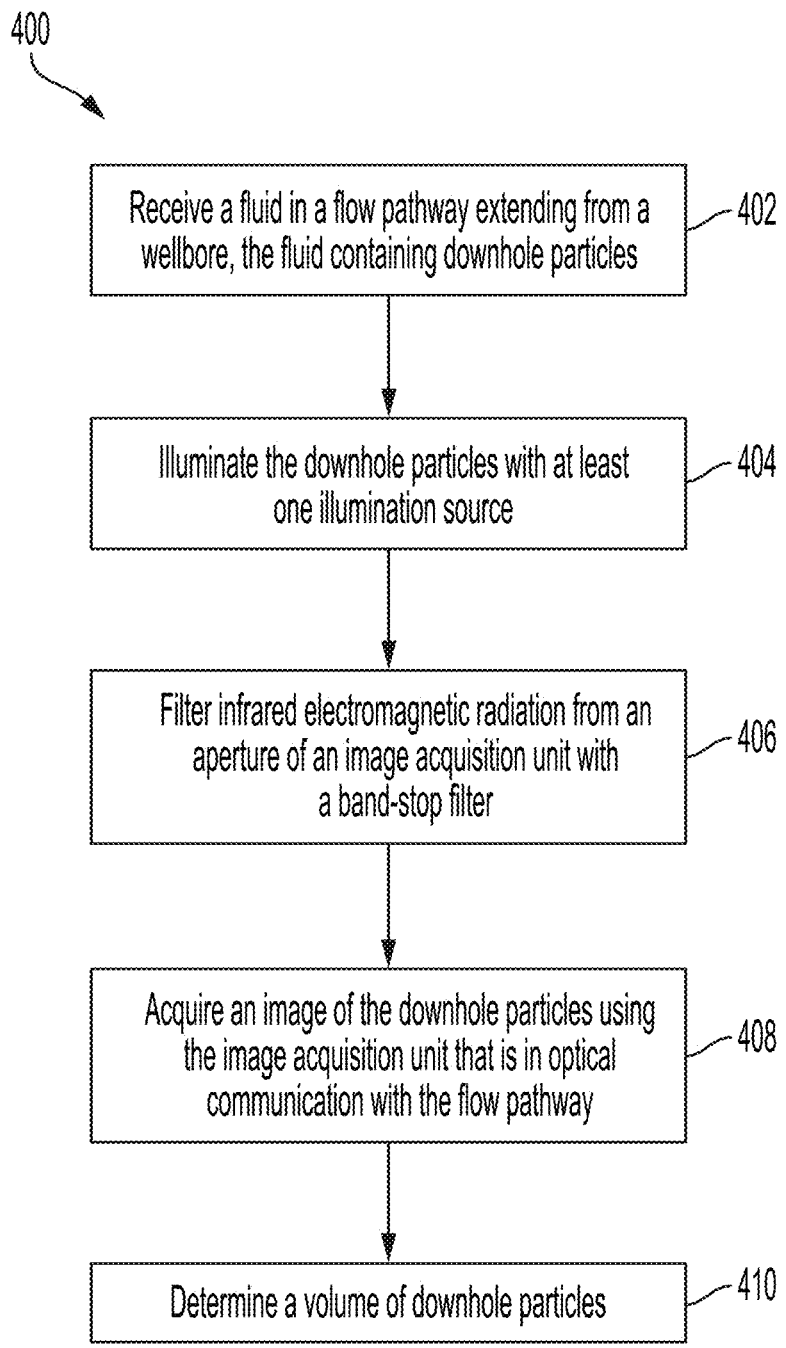
FIG. 4 is a flowchart of a process of evaluating and potentially altering downhole drilling operations based on an analysis of size and shape of particles in downhole cuttings, according to some aspects of the present disclosure.

FIG. 4 is a flowchart of a process 400 of evaluating and potentially altering downhole drilling operations based on an analysis of size and shape of particles in downhole cuttings, according to one example of the present disclosure. In some examples, the processing device 304 can implement some or all of the blocks shown in FIG. 4. Other examples can include more blocks, fewer blocks, different blocks, or a different order of the blocks than is shown in FIG. 4. The blocks of FIG. 4 are discussed below with reference to the components discussed above in relation to FIGS. 1, 2, and 3

At block 402, a portion of a drilling system 164, such as a shaker 238, may receive a fluid in a flow pathway extending from the wellbore 112. The fluid may contain drilling fluid and downhole particles 112 resultant from drilling performed by the drilling assembly 126 on the subterranean formation 114.

At block 404, the processing device 304 can cause the illumination source 322 to illuminate the downhole particles. The illumination source 322 may include a one or more light sources of varying electromagnetic radiation output wavelengths. The downhole particles may be illuminated with electromagnetic radiation of various wavelengths for a variety of purposes. For example, laser illumination may be used to illuminate the downhole particles for use in determining physical characteristics of the downhole particles by the image acquisition unit 320, while radar emissions may be used to judge the velocity of downhole particles. The laser illumination sources may enable determination of physical characteristics of downhole particles. The processing device 304 may compare changes in omitted vs refracted wavelength of laser light, which can be indicative of particles geometry being more rounded, rectangular, or triangular. In some examples, the downhole particles are separated from the drilling fluid at a shale shaker. The shale shaker may be a practical location within a drilling system to observe downhole particles because larger particles most useful for analysis may be separated from the drilling fluid and finer particles.

At block 406, the processing device 304 can control the image acquisition unit 320 to receive filtered infrared electromagnetic radiation at an aperture of the image acquisition unit 320. In some examples, the band-stop filter 330 may only enable transmission of a portion of the infrared spectrum through the aperture of the image acquisition unit 320. Use of the band-stop filter 330 may remove a need to shield the aperture of the image acquisition unit 320 from external light sources in the environment, such as sunlight, electric lights distinct from the illumination source 322, or any other ambient light source.

At block 408, the processing device 304 may control the image acquisition unit 320 to acquire the image 310 of the downhole particles from the flow pathway. In some examples, the processing device 304 may control the image acquisition unit 320 to acquire video data of the downhole particles or variations in deflected, measured wavelengths of light from suitable light sources, such as a laser.

At block 410, the processing device 304 may determine a volume of downhole particles based on deflections of the non-infrared wavelength light output observed by the image acquisition unit 320. Facial recognition engines, such as the three-dimensional face recognition engine 312, trained to evaluate geometries of downhole particles may be used to evaluate the volume of the downhole particles. In response to a determination that a difference between a measured volume and a projected volume exceeds an error threshold, the processing device 304 may output a notification of a downhole condition occurring. In response to a determination that a difference between a measured volume and a projected volume exceeds an error threshold, the processing device 304 may adjust a drilling operation based on the difference between the measured volume and the projected volume.

In some aspects, systems, methods, and non-transitory computer-readable mediums are provided according to one or more of the following examples:

As used below, any reference to a series of examples is to be understood as a reference to each of those examples disjunctively (e.g., "Examples 1-4" is to be understood as "Examples 1, 2, 3, or 4").

Example 1 is a system comprising: an image acquisition unit in optical communication with a flow pathway; at least one illumination source directable toward a shale shaker to emit a light output; a band-stop filter positionable at the image acquisition unit to block electromagnetic radiation of an infrared spectrum and to allow electromagnetic radiation of the light output from the at least one illumination source to reach the image acquisition unit; and an analysis device positionable to determine a volume of downhole particles on the shale shaker using deflections of the light output observed by the image acquisition unit.

Example 2 is the system of example 1, wherein the downhole particles comprise cuttings from a formation surrounding a wellbore, and wherein the analysis device is positionable to determine the volume of downhole particles based on detected sizes and velocities of the downhole particles.

Example 3 is the system of example 2, wherein the analysis device is positionable to determine a projected volume of cuttings returning to a surface during drilling of the wellbore.

Example 4 is the system of examples 1-3, wherein the at least one illumination source comprises a plurality of illumination sources of varying light output wavelengths, and wherein the band-stop filter is adjustable to block electromagnetic radiation outside of the varying light output wavelengths of the plurality of illumination sources.

Example 5 is the system of examples 1-4, wherein the image acquisition unit comprises a visible camera, a near-infrared camera, a mid-infrared camera, a far-infrared camera, or any combination thereof.

Example 6 is the system of examples 1-5, wherein the shale shaker is positionable to vibrate a shaker screen to separate the downhole particles from a fluid.

Example 7 is the system of examples 1-6, wherein the analysis device is positionable to, in response to a determination that a difference between a measured volume and a projected volume exceeds an error threshold, output a notification of a downhole condition occurring.

Example 8 is a method comprising: receiving a fluid in a flow pathway extending from a wellbore, the fluid containing downhole particles; illuminating the downhole particles with at least one illumination source emitting a light output; filtering infrared electromagnetic radiation from an aperture of an image acquisition unit with a band-stop filter; acquiring an image of the downhole particles using the image acquisition unit that is in optical communication with the flow pathway; and determining a volume of downhole particles using deflections of the light output observed by the image acquisition unit at a shale shaker.

Example 9 is the method of example 8, wherein the determined volume of the downhole particles is determined using detected sizes and velocities of the downhole particles.

Example 10 is the method of example 9, further comprising: determining a projected volume of downhole particles returning to a surface during a drilling of the wellbore.

Example 11 is the method of example 10, further comprising: outputting a notification of a downhole condition occurring in response to a determination that a difference between the determined volume of the downhole particles and the projected volume of the downhole particles exceeds an error threshold.

Example 12 is the method of examples 8-11, further comprising: adjusting the band-stop filter to block electromagnetic radiation outside of wavelengths of the light output of the at least one illumination source, wherein the at least one illumination source comprises a plurality of illumination sources.

Example 13 is the method of examples 8-12, wherein the image acquisition unit comprises a visible camera, a near-infrared camera, a mid-infrared camera, and a far infrared camera, or any combination thereof.

Example 14 is the method of examples 8-13, wherein the at least one illumination source comprises at least one laser.

Example 15 is a non-transitory computer-readable medium comprising program code that is executable by one or more processing devices for causing the one or more processing devices to: receive a fluid in a flow pathway extending from a wellbore, the fluid containing downhole particles; control at least one illumination source to emit a light output to illuminate the downhole particles, wherein the light output comprises a wavelength that is passed by a band-stop filter that filters infrared electromagnetic radiation from an aperture of an image acquisition unit; control the image acquisition unit that is in optical communication with the flow pathway to acquire an image of the downhole particles; and determine a volume of downhole particles using deflections of the light output observed by the image acquisition unit.

Example 16 is the non-transitory computer-readable medium of example 15, wherein the determined volume of the downhole particles is determined using detected sizes and velocities of the downhole particles.

Example 17 is the non-transitory computer-readable medium of example 16, further comprising program code that is executable by the processing device for causing the processing device to: determine a projected volume of downhole particles returning to a surface during a drilling of the wellbore.

Example 18 is the non-transitory computer-readable medium of example 17, further comprising program code that is executable by the processing device for causing the processing device to: output a notification of a downhole condition occurring in response to a determination that a difference between the determined volume of the downhole particles and the projected volume of the downhole particles exceeds an error threshold.

Example 19 is the non-transitory computer-readable medium of examples 15-18, wherein the image acquisition unit comprises a visible camera, a near-infrared camera, a mid-infrared camera, and a far infrared camera, or any combination thereof.

Example 20 is the non-transitory computer-readable medium of examples 15-19, wherein the at least one illumination source comprises at least one laser.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A system comprising:
   an image acquisition unit in optical communication with a flow pathway;
   at least one illumination source directable toward a shale shaker to emit a light output;
   a band-stop filter positionable at the image acquisition unit to block infrared wavelength electromagnetic radiation of the light output from reaching an aperture of the image acquisition unit, while allowing non-infrared wavelength electromagnetic radiation of the light output to reach the aperture of the image acquisition unit; and
   an analysis device positionable to determine a volume of downhole particles on the shale shaker using deflections of the non-infrared wavelength light output observed by the image acquisition unit.

2. The system of claim 1, wherein the downhole particles comprise cuttings from a formation surrounding a wellbore, and wherein the analysis device is positionable to determine the volume of downhole particles based on detected sizes and velocities of the downhole particles.

3. The system of claim 2, wherein the analysis device is positionable to determine a projected volume of cuttings returning to a surface during drilling of the wellbore.

4. The system of claim 1, wherein the at least one illumination source comprises a plurality of illumination sources of varying light output wavelengths, and wherein the band-stop filter is adjustable to block electromagnetic radiation outside of the varying light output wavelengths of the plurality of illumination sources.

5. The system of claim 1, wherein the image acquisition unit comprises a visible camera, a near-infrared camera, a mid-infrared camera, a far-infrared camera, or any combination thereof.

6. The system of claim 1, wherein the shale shaker is positionable to vibrate a shaker screen to separate the downhole particles from a fluid.

7. The system of claim 1, wherein the analysis device is positionable to, in response to a determination that a difference between a measured volume of downhole particles and a projected volume of downhole particles exceeds an error threshold, output a notification of a downhole condition occurring.

8. A method comprising:
   receiving a fluid in a flow pathway extending from a wellbore, the fluid containing downhole particles;
   illuminating the downhole particles with at least one illumination source emitting a light output;
   blocking, with a band-stop filter, electromagnetic radiation of an infrared wavelength from an aperture of an image acquisition unit with in optical communication with the flow pathway;
   acquiring an image of the downhole particles using the image acquisition unit; and
   determining a volume of downhole particles using deflections of non-infrared wavelengths of the light output observed by the image acquisition unit at a shale shaker.

9. The method of claim 8, wherein the determined volume of the downhole particles is determined using detected sizes and velocities of the downhole particles.

10. The method of claim 9, further comprising:
    determining a projected volume of downhole particles returning to a surface during a drilling of the wellbore.

11. The method of claim 10, further comprising:
    outputting a notification of a downhole condition occurring in response to a determination that a difference between the determined volume of the downhole particles and the projected volume of the downhole particles exceeds an error threshold.

12. The method of claim 8, further comprising:
    adjusting the band-stop filter to block electromagnetic radiation outside of wavelengths of the light output of the at least one illumination source, wherein the at least one illumination source comprises a plurality of illumination sources.

13. The method of claim 8, wherein the image acquisition unit comprises a visible camera, a near-infrared camera, a mid-infrared camera, a far infrared camera, or any combination thereof.

14. The method of claim 8, wherein the at least one illumination source comprises at least one laser.

15. A non-transitory computer-readable medium comprising program code that is executable by one or more processing devices for causing the one or more processing devices to:
    control at least one illumination source to emit a light output to illuminate downhole particles contained in a fluid in a flow pathway extending from a wellbore, wherein the light output comprises a wavelength that is passed by a band-stop filter that blocks infrared wavelength electromagnetic radiation from an aperture of an image acquisition unit in optical communication with the flow pathway;
    control the image acquisition unit to acquire an image of the downhole particles; and
    determine a volume of downhole particles using deflections of non-infrared wavelengths of the light output observed by the image acquisition unit.

16. The non-transitory computer-readable medium of claim 15, wherein the determined volume of the downhole particles is determined using detected sizes and velocities of the downhole particles.

17. The non-transitory computer-readable medium of claim 16, further comprising program code that is executable by the processing device for causing the processing device to:
    determine a projected volume of downhole particles returning to a surface during a drilling of the wellbore.

18. The non-transitory computer-readable medium of claim 17, further comprising program code that is executable by the processing device for causing the processing device to:
    output a notification of a downhole condition occurring in response to a determination that a difference between the determined volume of the downhole particles and the projected volume of the downhole particles exceeds an error threshold.

19. The non-transitory computer-readable medium of claim 15, wherein the image acquisition unit comprises a visible camera, a near-infrared camera, a mid-infrared camera, a far infrared camera, or any combination thereof.

20. The non-transitory computer-readable medium of claim 15, wherein the at least one illumination source comprises at least one laser.

* * * * *